(12) United States Patent
Nesper et al.

(10) Patent No.: US 7,674,280 B2
(45) Date of Patent: Mar. 9, 2010

(54) IMPLANT FOR FIXING ADJACENT BONE PLATES

(75) Inventors: Markus Nesper, Tuttlingen (DE);
Klaus-Dieter Steinhilper, Tuttlingen (DE); Dieter Weisshaupt, Immendingen (DE); Karl-Dieter Lerch, Witten (DE)

(73) Assignee: Aesculap AG, Tuttlingen (DE)

( * ) Notice: Subject to any disclaimer, the term of this patent is extended or adjusted under 35 U.S.C. 154(b) by 1212 days.

(21) Appl. No.: 10/731,284

(22) Filed: Dec. 9, 2003

(65) Prior Publication Data

US 2004/0116961 A1   Jun. 17, 2004

Related U.S. Application Data

(63) Continuation of application No. PCT/EP02/05652, filed on May 23, 2002.

(30) Foreign Application Priority Data

Jun. 15, 2001  (DE) .................. 101 28 918

(51) Int. Cl.
*A61B 17/80*  (2006.01)
(52) U.S. Cl. .............. 606/297; 606/216; 606/903; 606/74
(58) Field of Classification Search .......... 606/69–72, 606/280–299, 151, 215–218, 74–75, 902–906
See application file for complete search history.

(56) References Cited

U.S. PATENT DOCUMENTS

| 261,501 | A | * | 7/1882 | Vandermark ............... 24/115 R |
| 1,669,537 | A | * | 5/1928 | Schaffer ........................ 24/713 |
| 3,357,432 | A | * | 12/1967 | Sparks ........................ 606/151 |
| 4,201,215 | A | * | 5/1980 | Crossett et al. ............. 606/216 |
| 4,398,655 | A | * | 8/1983 | Perry .......................... 224/191 |
| 5,072,738 | A | * | 12/1991 | Wonder et al. .............. 128/888 |
| 5,356,412 | A | * | 10/1994 | Golds et al. ................... 606/74 |
| 5,474,572 | A | * | 12/1995 | Hayhurst ..................... 606/232 |
| 5,584,856 | A | * | 12/1996 | Jameel et al. ................ 606/220 |
| 5,620,452 | A | * | 4/1997 | Yoon .......................... 606/151 |
| 5,800,436 | A |  | 9/1998 | Lerch |
| 6,010,525 | A | * | 1/2000 | Bonutti et al. .............. 606/232 |

(Continued)

FOREIGN PATENT DOCUMENTS

DE   196 03 887   8/1997

(Continued)

*Primary Examiner*—Thomas C Barrett
*Assistant Examiner*—James L. Swiger
(74) *Attorney, Agent, or Firm*—Lipsitz & McAllister, LLC

(57) ABSTRACT

In order to provide an implant for fixing adjacent bone plates, in particular cranial bone plates, which has an inner abutment element by means of which a separation gap between the bone plates can be overlapped at a bone plate inner side and has an outer abutment element for overlapping the separation gap at a bone plate outer side lying opposite the bone plate inner side and which is easy for a surgeon to use and by means of which the bone plates may be securely fixed, it is proposed that at least one tension band is guided displaceably through the outer abutment element, by means of which, when a tensile stress is exerted, the inner abutment element and the outer abutment element are mutually braceable, and that the at least one tension band is fixable on the outer abutment element.

22 Claims, 6 Drawing Sheets

U.S. PATENT DOCUMENTS

| | | | |
|---|---|---|---|
| 6,045,551 A * | 4/2000 | Bonutti | 606/60 |
| 6,051,007 A * | 4/2000 | Hogendijk et al. | 606/151 |
| 6,068,591 A * | 5/2000 | Bruckner et al. | 600/30 |
| 6,068,631 A | 5/2000 | Lerch | |
| 6,099,547 A * | 8/2000 | Gellman et al. | 606/198 |
| 6,228,087 B1 * | 5/2001 | Fenaroli et al. | 606/73 |
| 6,238,395 B1 | 5/2001 | Bonutti | |
| 6,508,828 B1 * | 1/2003 | Akerfeldt et al. | 606/215 |
| 6,921,401 B2 * | 7/2005 | Lerch et al. | 606/72 |
| 2002/0156475 A1 | 10/2002 | Lerch et al. | |

FOREIGN PATENT DOCUMENTS

| | | |
|---|---|---|
| DE | 199 52 359 | 3/2001 |

* cited by examiner

IMPLANT FOR FIXING ADJACENT BONE PLATES

The present disclosure relates to the subject matter disclosed in German application No. 101 28 918.9 of Jun. 15, 2001 and international application PCT/EP 02/05652 of May 23, 2002, which are incorporated herein by reference in their entirety and for all purposes.

BACKGROUND OF THE INVENTION

The invention relates to an implant for fixing adjacent bone plates, in particular cranial bone plates, having an inner abutment element by means of which a separation gap between the bone plates can be overlapped at a bone plate inner side and having an outer abutment element for overlapping the separation gap at a bone plate outer side lying opposite the bone plate inner side.

For brain surgery a craniotomy has to be performed in order to gain access to the brain tissue that is to be operated on. For this purpose, one or more bone plates are sawn out of the skull. On completion of the brain surgery these bone plates have to be reinserted and fixed to the bone plates of the rest of the skull. For this purpose, suitable implants are provided, which remain in the body of the patient.

SUMMARY OF THE INVENTION

In accordance with the present invention, an implant for fixing adjacent bone plates is provided, which is easy for the surgeon to use and by means of which the bone plates may be securely fixed.

This is achieved in accordance with the invention in that at least one tension band is guided displaceably through the outer abutment element, by means of which, when a tensile stress is exerted, the inner abutment element and the outer abutment element are mutually braceable, and that the at least one tension band is fixable to the outer abutment element.

Through the tightening of a tension band the inner abutment element and the outer abutment element may be moved towards one another and mutually braced so that the adjacent bone plates are fixed to one another. This tensioned position in turn may be secured by fixing the tension band to the outer abutment element. The bracing may therefore be effected easily by the surgeon without the requirement for an additional application instrument.

A tension band is easy for the surgeon to manipulate because it has a sufficiently large width for grasping and exerting tension.

A tension band moreover provides enough surface area to be able to effect fixing to the outer abutment element. In particular, for securing the fixed position of the bone plates hook elements are provided, which may penetrate the tension band and therefore secure this fixed position.

Furthermore, the implant according to the invention is also easy to manufacture since the inner abutment element and the outer abutment element may be manufactured separately from the tension band and the connection between tension band and abutment elements may easily be produced by threading the former through the latter.

The implant according to the invention is moreover insertable in an advantageous manner: during insertion of a bone plate into a cranial recess the inner abutment element may be held by means of the tension band until the desired relative positioning of the bone plates is achieved. It is then possible afterwards to guide the outer abutment element by means of the tension band and hence effect the bracing.

A tension band may in said case, depending on the application, be manufactured from an absorbable or non-absorbable material. Suitable absorbable materials are, in particular, synthetic materials or organic materials. Suitable non-absorbable materials are plastics materials such as PEEK or also metal materials such an titanium or other biologically compatible materials.

It is quite particularly advantageous when the width of the at least one tension band is greater than its height and in particular is substantially greater, e.g. at least five times greater. This then provides a corresponding surface area, which is easier for a surgeon to grasp and which allows easy fixing of the tension band to the outer abutment element by means of hook elements.

In said case, in order further to facilitate handling and obtain a secure fixing to the outer abutment element, the width of the at least one tension band is in the region of between 25% and 75% of a width dimension of an abutment element. In particular, in said case the width is in the region of ca. half of this width dimension, which in the case of a round disk-shaped abutment element is the diameter.

In particular, it is provided that the at least one tension band is of a flexibly bendable design so as to allow the two abutment elements to be drawn towards one another and hence braced relative to one another.

It is provided that the at least one tension band is held on the inner abutment element in order during the bracing to provide a fixed point, i.e. ensure that the tension band no longer moves relative to the inner abutment element.

It may then in principle be provided that the at least one tension band is fastened to the inner abutment element, i.e. is fixed invariably with regard to its holding point thereon.

It is however quite particularly advantageous when a tension band is passed through the inner abutment element and in said case the tension band is held on the inner abutment element by means of a tension band bend. Thus, the tension band may be fixed on the inner abutment element, wherein however said fixing is variable. Thus, on the one hand, manufacture is facilitated and, on the other hand, because of the holding by means of a tension band bend a high degree of certainty that the inner abutment element and the tension band will not detach from one another is achieved.

From the point of view of manufacture, it is advantageous when the inner abutment element has two spaced-apart openings for passing the tension band through. Between the openings a kind of bridge is then formed, which holds, i.e. forms a bearing surface for, the tension band bend.

In said case, the openings are advantageously so disposed and designed, i.e. the bridge element is also correspondingly so disposed and designed, that a first tension band region and a second tension band region, between which a tension band bend is formed, during penetration of the separation gap are alignable substantially parallel to one another. This prevents the tension band bends from possibly exerting transverse forces upon the bone plates and, when tension is exerted upon the at least one tension band, possibly shifting the bone plates towards one another.

In order to provide a uniform bearing surface for the adjacent bone plates, the openings are advantageously disposed substantially mirror-symmetrically relative to a center of the inner abutment element.

It is in said case advantageous when the spacing of the openings is less than ca. an eighth of a width dimension of the inner abutment element. In the case of a circular abutment element, this width dimension is the diameter. It is thereby possible to ensure that the separation gap, through which the tension band has to be passed, does not become too large and, on the other hand, achieve parallel guidance of appropriate tension band regions.

In said case, edges of the openings are advantageously rounded off to prevent damage to the tension band.

It is further advantageous when the outer abutment element has one or more openings, through which in each case one longitudinal end of a tension band is passable. Thus, by means of the at least one tension band the outer abutment element may be fixed relative to the inner abutment element and so, in turn, adjacent bone plates may be fixed between the two abutment elements.

In order by tightening the tension band to be able to effect a bracing of the two abutment elements and in addition move the outer abutment element relative to the inner abutment element, an opening has a deflection edge for deflecting a tension band, so that a tensile force is exertable upon the tension band transversely relative to a direction of spacing between inner abutment element and outer abutment element. In particular, in said case the deflection edge is rounded off in order to guarantee good guidance of the tension band in the opening and, on the other hand, prevent damage to the tension band.

Advantageously in said case the opening or openings are disposed and designed in such a way that the at least one tension band is positioned substantially at right angles to the abutment element in the separation gap in order thereby to prevent the tension band from exerting transverse forces upon the bone plates and to be able to keep the size of the separation gap small.

A fixation of the bone plates between the abutment elements is easily achievable when a tensile force with a transverse component in a first direction is exertable upon a first tension band end and a tensile force with a transverse component in an opposite direction is exertable upon a second tension band end. By a relative pulling of the two tension band ends apart from one another, the outer abutment element is then displaced in the direction of the inner abutment element and a bracing and hence fixation of the bone plates between the two abutment elements is effected.

An implant according to the invention may easily be manufactured when the first tension band end and the second tension band end are formed on the same tension band, i.e. when the tension band is looped through the inner abutment element and then the respective ends are conveyed in opposite directions.

The fixation of the bone plates may easily be secured when the at least one tension band may be hooked in relative to the outer abutment element. The tension band provides a large surface area for the engagement and in particular for the penetration of hook elements in order thereby to enable the fixing of the tension band relative to the outer abutment element.

In particular, it is in said case advantageous when a hook element has an inclined flank and a steep flank, wherein the steep flank is arranged facing a pulling end of the at least one tension band. In said case, the steep flank is in particular designed in such a way that, when the tension band is hooked in, the steep flank is substantially at right angles to the tension band. A hook element then has a substantially triangular cross section, wherein the steep flank is the one at a steeper angles relative to a vertical direction of the triangle. Given a corresponding arrangement of the steep flank facing the pulling end, it is guaranteed that during the hooking-in operation the tension is not reduced, since hooking-in of the hook-connection face of a hook element is effected in a region of the tension band situated closer to the inner abutment element, on which the tension band is held, and so the tensioning force is maintained while the hooking-in operation is effected. On the other hand, however, it is thereby also ensured that the forces acting upon the tension band do not increase, with the result that e.g. a relative positioning of the bone plates desired by the surgeon is not destroyed by increased forces during the hooking-in operation.

In a variant of a form of construction the hook element or elements are disposed on the outer abutment element. The surgeon may then easily effect the fixed position of the bone plates by hooking-in of the tension band on the outer abutment element. In particular, in said case a row of spaced-apart hook elements is provided for effecting a fixation over a large surface area.

It may in said case be provided that the hook element or elements are disposed on an outer surface of the outer abutment element. In particular, in said case hook tips are directed away from an outer surface of the outer abutment element.

It may alternatively or additionally be provided that the hook element or elements are disposed in an opening for passing the at least one tension band through. In this variant, fixing of the tension band is effected in the opening. Hook tips are then orientated transversely of a direction of spacing between inner abutment element and outer abutment element.

In a further form of construction a fixation cap is provided for mounting on the outer abutment element, wherein the tension band is fixable between the outer abutment element and the fixation cap. It is then possible to effect fixation of the bone plates and secure this position by mounting the fixation cap.

It is in said case quite particularly advantageous when the fixation cap comprises a bridge element, which is insertable into the separation gap. This bridge element then effects an additional fixation in the separation gap and, on the other hand, the separation gap may be filled by the bridge element.

The bridge element is advantageously insertable between opposite tension band regions into the separation gap, thereby achieving an additional securing of the tensioned position of the tension band.

In a variant of a form of construction there are formed on the bridge element transverse tabs, which are elastically movable at right angles to the direction of spacing between inner abutment element and outer abutment element.

Thus, in the inserted state of the bridge element, when this is suitably adapted to the outer abutment element, an elastic force may be exerted by the bridge element upon the abutment element, which effects an additional fixing of the fixation cap on the outer abutment element, so that in turn a good securing of the fixation of the bone plates may be achieved.

In order to fix the tension band between the outer abutment element and the fixation cap, the fixation cap and/or the outer abutment element is provided with one or more hook elements and the outer abutment element and/or the fixation cap is provided with corresponding openings for receiving the hook element or elements. It may thereby be guaranteed that the hook elements penetrate and hence securely hold the tension band. The openings then ensure that the hook elements, which project relative to the tension band, are received. Furthermore, an additional fixing may be achieved by the engagement of the hook elements into the openings.

The following description of preferred forms of construction is used in connection with the drawings to explain the invention in detail.

DETAILED DESCRIPTION OF THE INVENTION

Figure 1:
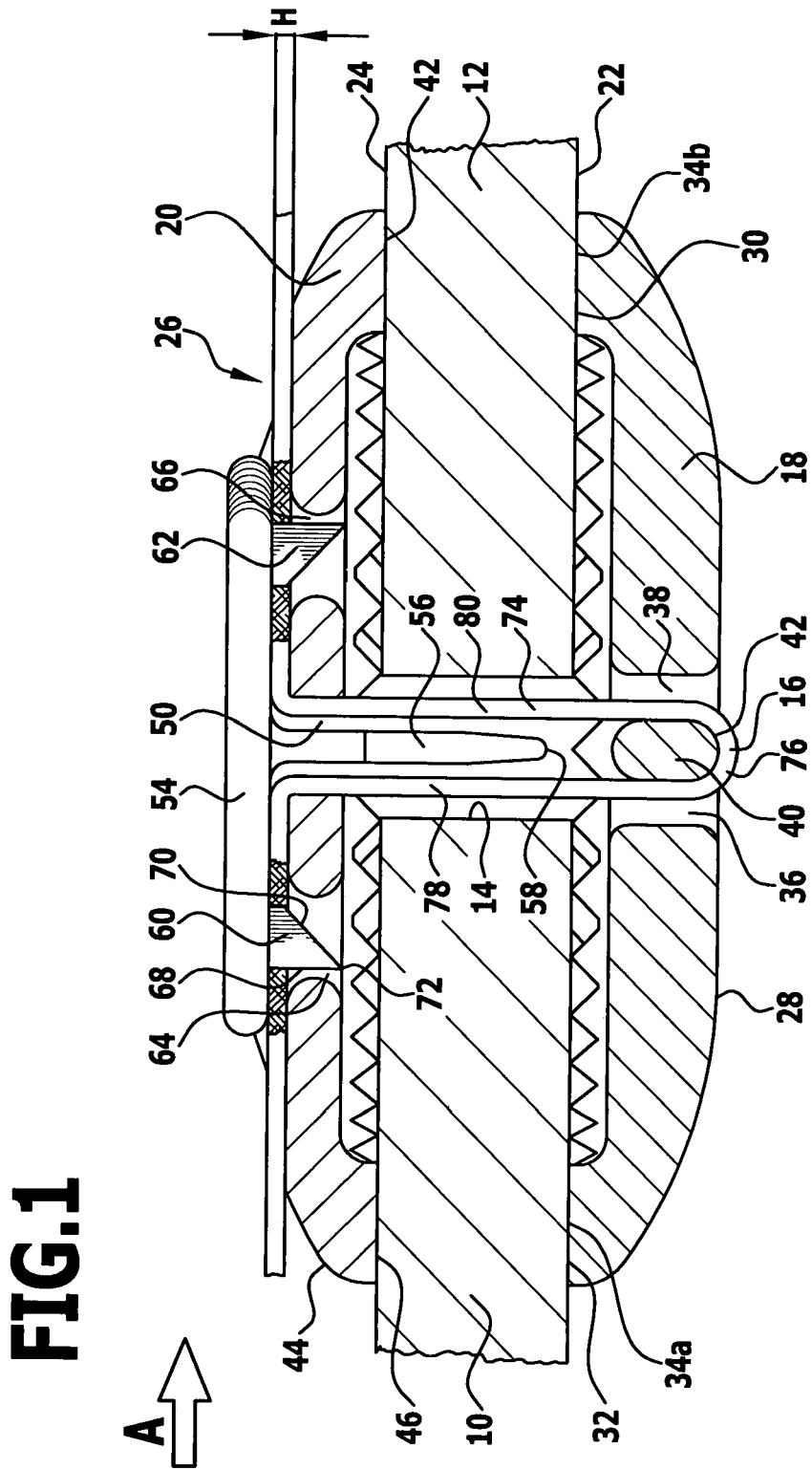
FIG. 1 a side sectional view of a first embodiment of an implant according to the invention for fixing adjacent bone plates, wherein a fixed position is shown.
Figure 2:
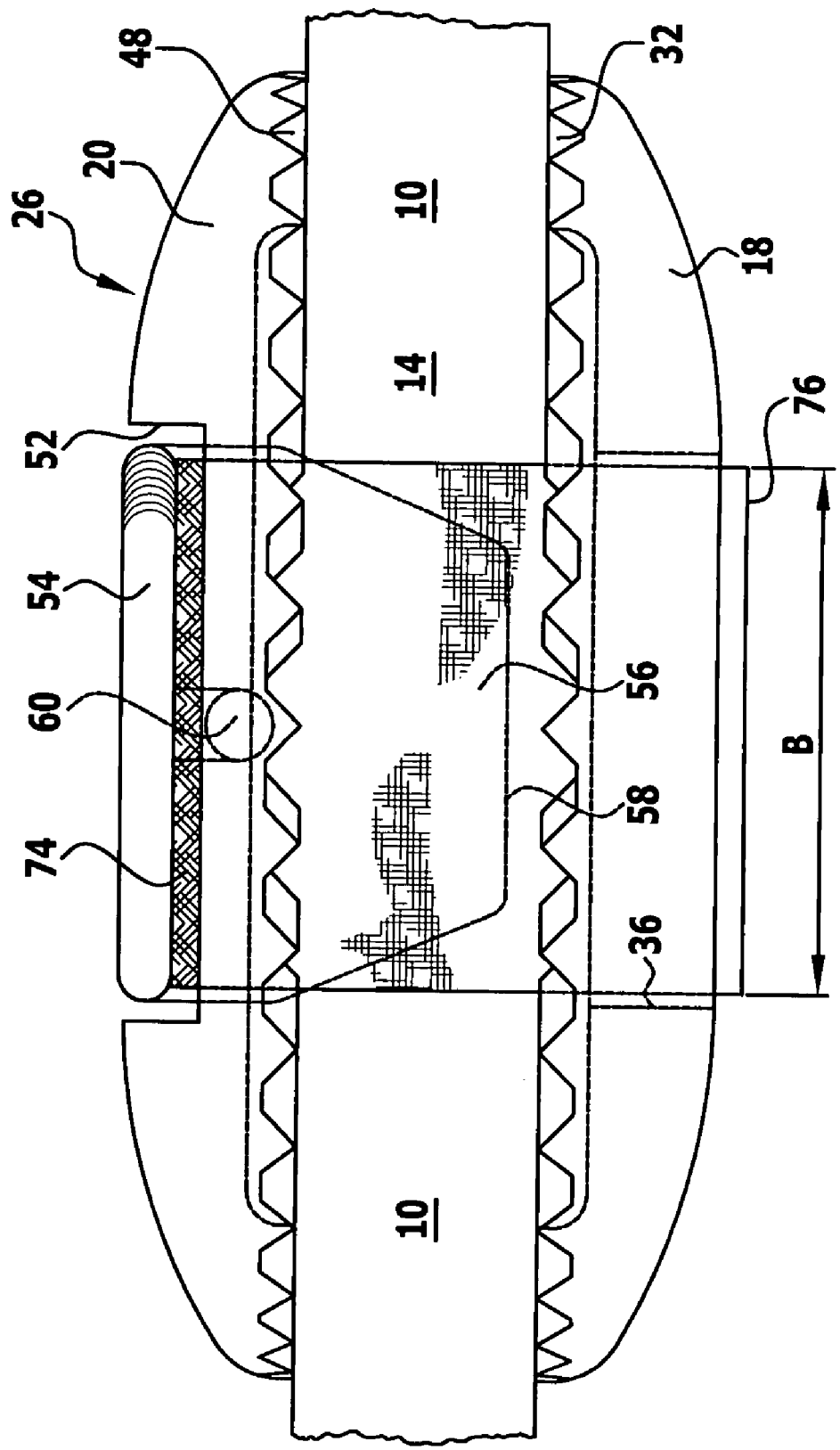
FIG. 2 a sectional view in direction A of the implant according to FIG. 1.

By means of an implant according to the invention adjacent bone plates 10, 12 may be fixed. For example, for brain surgery the cranium is opened by removing one or more pieces of bone. At the end of surgery the corresponding bone pieces are reinserted, for which purpose the adjacent bone plates 10 and 12 then have to be positioned relative to one another and fixed in an appropriate final position. In said case, between the bone plates 10 and 12 a separation gap 14 is formed, through which connecting means 16 for the connection between an inner abutment element 18 and an outer abutment element 20 may be passed. If, for example, the bone plates 10 and 12 are cranial bone plates, then the inner abutment element 18 is positioned on bone plate inner sides 22 facing the cranium interior and the outer abutment element 20 is positioned on an opposite bone plate outer side 24.

In the first embodiment of an implant according to the invention for fixing adjacent bone plates 10, 12, which is illustrated in FIG. 1 and denoted there as a whole by 26, the inner abutment element 18 is of a disk-shaped design, wherein it has in particular a circular cross section. It is made of a plastics material well-tolerated by the body, an absorbable plastics material or a metal. An outer surface 28 of the inner abutment element is curved in a convex manner. An opposite surface 30 to this outer surface 28 is provided with a toothed wheel ring 32, which is used for an improved grip on the bone plates 10 and 12.

By means of the inner abutment element 18 the separation gap 14 is overlappable, so that the toothed wheel ring 32 lies in a sub-region 34a against the bone plate 10 and in an, in particular, opposite sub-region 34b against the bone plate 12.

Outside of the toothed wheel ring 32 the surface 30 is set back relative to tooth tips.

Formed in the inner abutment element 18 in a central region are two spaced-apart slot-shaped through-openings 36, 38, which extend between the surfaces 30 and 28. They are separated by a bridge element 40. This bridge element 40 has rounded-off edges 42 in particular facing the outer surface 28.

The outer abutment element 20 is likewise of a disk-shaped design and has in particular a circular cross section, wherein the outer dimensions of the outer abutment element 20 substantially correspond to those of the inner abutment element 18. It is, like the inner abutment element 18, made of a plastics material well-tolerated by the body, an absorbable plastics material or metal. It likewise has a convex outer surface 44 and an opposite surface 46, which is provided with a toothed wheel ring 48 corresponding to the toothed wheel ring 32 of the inner abutment element 18.

Formed in the inner abutment element in a central region is a slot-shaped through-opening 50, through which the connecting means 16 are passable.

In the outer surface 44 there is provided adjacent to the opening 50 a square recess 52, which is used to receive a fixation cap 54. A bridge element 56 is in said case disposed in a central region and, in particular, integrally on the fixation cap 54 and is of a wedge-shaped design at its front end 58. This bridge element 56 may be inserted into and hence at least partially fill the separation gap 14 between the bone plates 10 and 12 and the connecting means 16 may be fixed relative to the separation gap 14 in the manner described in greater detail below.

The fixation cap 54 has, symmetrically relative to the bridge element 56, opposing hook elements 60, 62, which may engage into corresponding through-openings 64, 66 of the outer abutment element 20. A hook element 60, 62 in said case has a steep flank 68 and an inclined flank 70, so that a hook element 60, 62 is of a triangular design. Thus, once the fixation cap 54 has been inserted into the recess 52, a tip 72 of a hook element 60, 62 points in the direction from the outer surface 44 to the surface 46, wherein the inclined flank 70 faces the central region of the outer abutment element 20, i.e. in particular faces the bridge element 56, while the steep flank 68 is disposed remote from this central region.

The connecting means 16 are formed by a tension band 74, which is elastically bendable. This tension band may be made of an absorbable or non-absorbable material. At the inner abutment element 18 the tension band is held in the openings 36, 38 on the bridge element 40 by means of a tension band bend 76, which is adjoined in each case by a first tension band region 78 and a second tension band region 80, which penetrate the separation gap 14. The first tension band region 78 is deflected at the opening 50, which for this purpose has in particular rounded-off edges, and extends substantially parallel to the outer surface 44 of the outer abutment element 20. In a corresponding manner the second tension band region 80 is likewise deflected and likewise extends parallel to the outer surface 44 of the outer abutment element 20. Corresponding ends of the tension band 74, which are associated with the first tension band region 78 and the second tension band region 80, are in said case situated remote from one another and the bridge element 56 is situated between these ends.

In the separation gap 14 the two tension band regions 78 and 80 are aligned substantially parallel to one another.

The tension band 74 is fixed relative to the inner abutment element 18 and the outer abutment element 20 in that the hook elements 60, 62 hook into the tension band 74 and these hook elements 60, 62 then engage further into the associated openings 64, 66 of the outer abutment element 20. By said means a fixation of adjacent bone plates 10, 12 by means of the implant 26 may be achieved.

The implant 26 according to the invention operates in the following manner:

The tension band 74 is looped by means of the through-openings 36 and 38 through the inner abutment element 18. The tension band in said case has a width B which is considerably greater than its height H. It is moreover looped through the outer abutment element 20 through the opening 50 thereof, in which case a surgeon may then grasp the respective ends of the tension band 74.

The bone plates 10 and 12 and the abutment elements 18 and 20 are positioned relative to one another in such a way that, firstly, the tension band 74 with its first tension band region 78 and its second tension band region 80 penetrates the separation gap 14, the inner abutment element 18 lies against the bone plate inner side 22 and overlaps the separation gap 14, and the outer abutment element 20 lies against the bone plate outer side 24 and likewise overlaps the separation gap 14. A surgeon then exerts tension upon each of the two ends of the tension band 74, which are associated in each case with the tension band regions 78 and 80, or holds one end fast and exerts tension upon the other end. In particular, for this purpose the tension band 74 is in each case folded over and conveyed parallel to the outer abutment element 20, so that the surgeon may exert upon the respective ends tensile forces in opposing directions in opposite ends. By virtue of such a tightening of the band the abutment elements 18 and 20 are drawn towards one another so as to achieve a secure fixation of the bone plates 10 and 12 between the abutment elements 18 and 20. The fixation cap 54 is then inserted into the recess 52, wherein the bridge element 56 engages into the separation gap 14. Thus, the tension band 74 is fixed in the separation gap 14 and the separation gap 14 is also at least partially filled by the bridge element 56.

During mounting of the fixation cap 54 the hook elements 60, 62 simultaneously engage into the tension band 74 and form a hooked connection therewith. The hook elements 60 and 62 engage into the associated openings 64 and 66. Consequently, the tension band 74 is fixed to the outer abutment element 20 and so, in turn, the fixed position of the bone plates 10 and 12 between the outer abutment element 20 and the inner abutment element 18 is secured.

The hook elements 60, 62 penetrate the tension band 74, i.e. the steep flank 68 has a height that is greater than the height H of the tension band 74. The designing of a hook element 60, 62 with the arrangement of the inclined flank 70 facing the opening 50 and the steep flank 68 facing the end of the tension band 74 in said case guarantees the forming of a hooked connection with simultaneous securing of the tensioned position.

The width B of the tension band is in the region of between ca. 25% and 75% of the diameter of the outer abutment element 20 and/or inner abutment element 18. Firstly, this makes it easy for the surgeon to grasp the tension band. Secondly, a large surface are is provided for hooked connections by means of the hook elements 60 and 62.

It may also be provided that, instead of a hook element 60 and/or 62, a row of hook elements is provided. It may moreover alternatively be provided that the hook elements are formed on the outer abutment element 20 and the fixation cap 54 then has corresponding openings.

Figure 3:
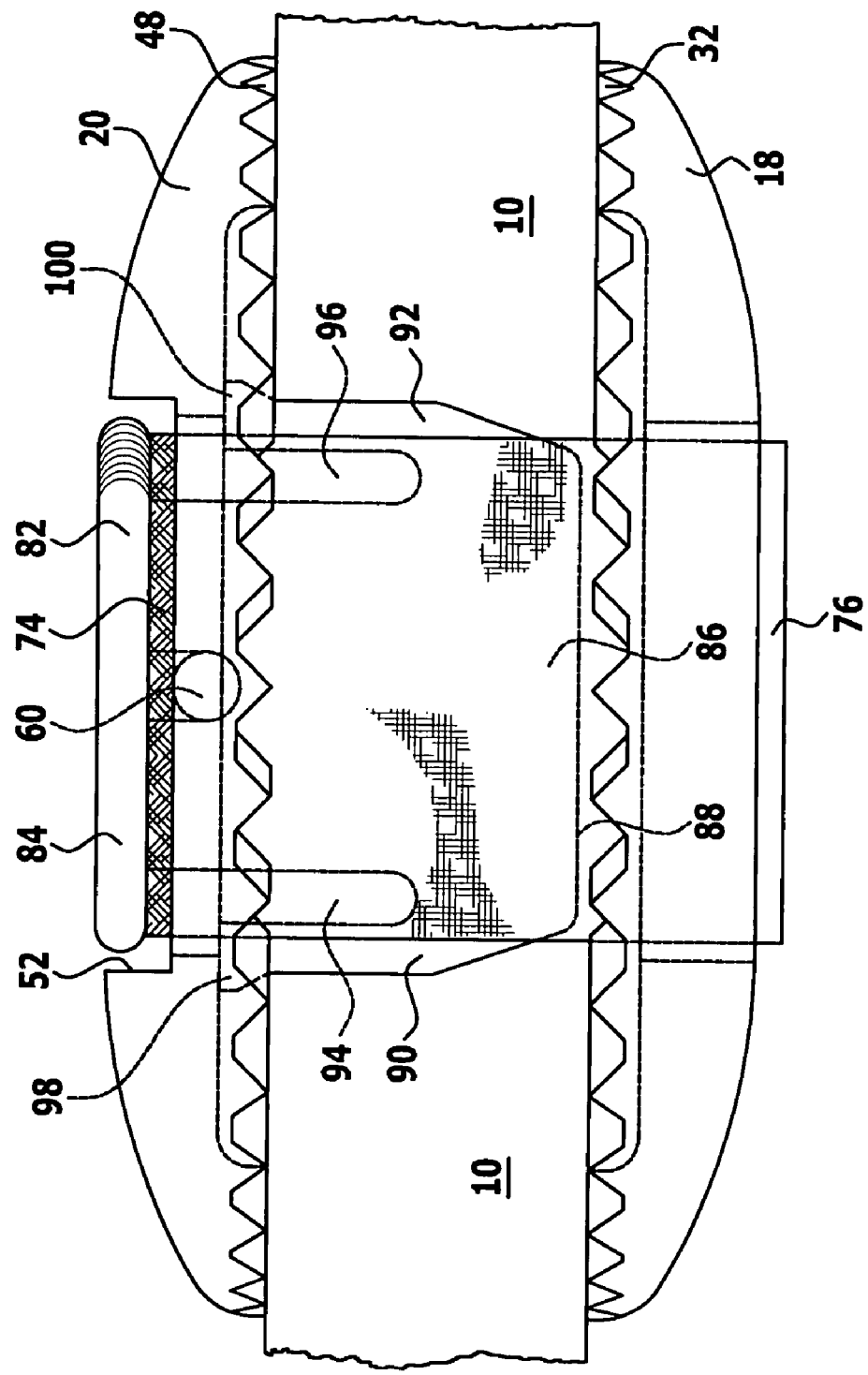
FIG. 3 a variant of the embodiment according to FIGS. 1 and 2 in a sectional view in the direction A.

A variant of the first embodiment 26, which is illustrated in FIG. 3, differs essentially in a different design of a fixation cap 82. Otherwise, the corresponding implant is designed and operates in an identical manner to that described above. Identical elements of the implant according to FIG. 3 therefore bear the same reference characters as for the implant 26.

The fixation cap 82 comprises a round cover disk 84, on which a bridge element 86 is integrally formed. This bridge element at its front end 88 is of a wedge-shaped design.

On the bridge element 86 opposite-lying transverse tabs 90, 92 are formed by respective slot-shaped recesses 94, 96, which extend substantially at right angles to the cover disk 84. On ends facing the cover disk 84 the transverse tabs 90, 92 are provided with retaining heads 98, 100.

By virtue of the recesses 94 and 96 the transverse tabs 90 and 92 respectively are movable transversely relative to the surface normal of the cover disk 84, i.e. in the region of the transverse tabs 90, 92 the width of the bridge element 86 may be reduced. This reduction of the width requires an expenditure of force for elastic deformation of the bridge element 86. The bridge element 86 may therefore be pushed through the opening 50 into the separation gap 14, wherein however the transverse tabs 90, 92 are bent elastically in the direction of the centrical axis of the cover disk 84. Once the cover disk 84 has been mounted and hooked in the tension band 74, the transverse tabs 90, 92 in the opening 50 then in turn exert a force upon the outer abutment element 20, wherein the retaining heads 98, 100 ensure reliable retention. The bridge element 86 and hence the fixation cap 82 are therefore additionally, besides the engagement of the hook elements 60, 62 into the associated openings 64, 66, braced with the outer abutment element 20.

Figure 4:
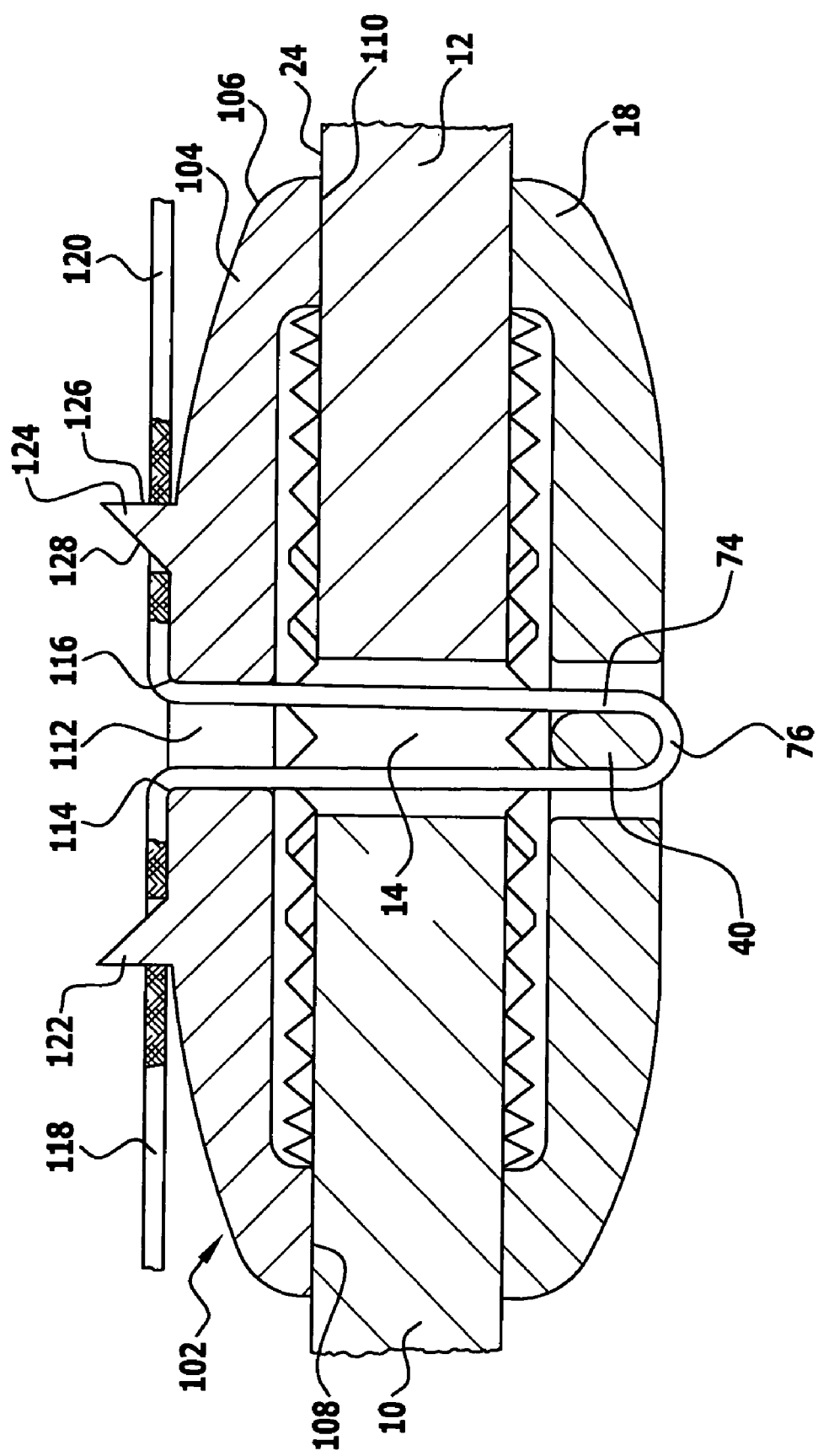
FIG. 4 a sectional view of a second embodiment of an implant according to the invention for fixing adjacent bone plates.

In a second embodiment, which is denoted as a whole by 102 in FIG. 4, the inner abutment element 18 is in principle of an identical construction to that described above. Identical reference characters are therefore used.

In the implant 102 an outer abutment element 104 is provided, which has a convex outer surface 106 and, remote therefrom, a surface 108 for resting against a bone plate outer side 24. This surface 108 is provided with a toothed wheel ring 110.

In a central region the outer abutment element 104 has a slot-shaped through-opening 112, through which the tension band 74 is passable. By means of the opening 112 deflection edges 114, 116 are formed, which are in particular rounded off, for changing the direction of the tension band from a direction substantially parallel to the separation gap 14 to a direction at right angles thereto. By exerting tension upon the respective ends 118 and 120 of the tension band 74 and/or by holding one end fast and exerting tension upon the other end, i.e. by tightening the tension band 74, the inner abutment element 18 and the outer abutment element 104 are drawn towards one another and the bone plates 10 and 12 situated therebetween may be securely fixed.

On its outer surface 106 the outer abutment element 104 has hook elements 122, 124, which are disposed in particular symmetrically relative to the opening 112 and are each associated with one end 118, 120 of the tension band 74. A steep flank 126 of a hook element 122 and/or 124 is in said case directed away from the opening 112, while an inclined flank 128 faces the opening 112.

After tightening of the tension band, the tension band may then be hooked into the respective hook elements 122, 124 in order thereby to secure the fixation of the bone plates 10 and 12 by means of the abutment elements 18 and 104.

Figure 5:
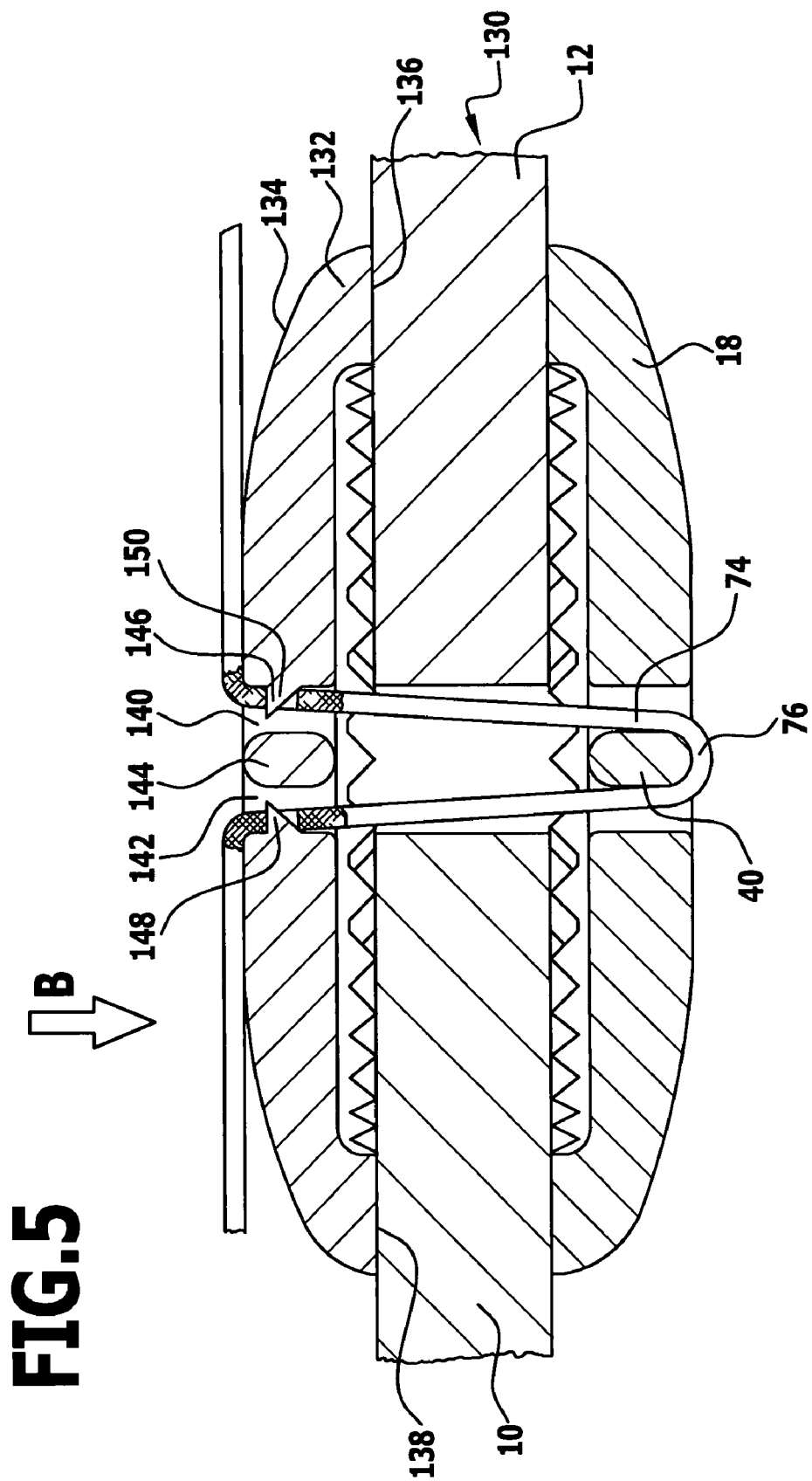
FIG. 5 a sectional view of a third embodiment of an implant according to the invention for fixing adjacent bone plates and FIG. 6 a plan view in direction B of the implant according to FIG. 5.
Figure 6:
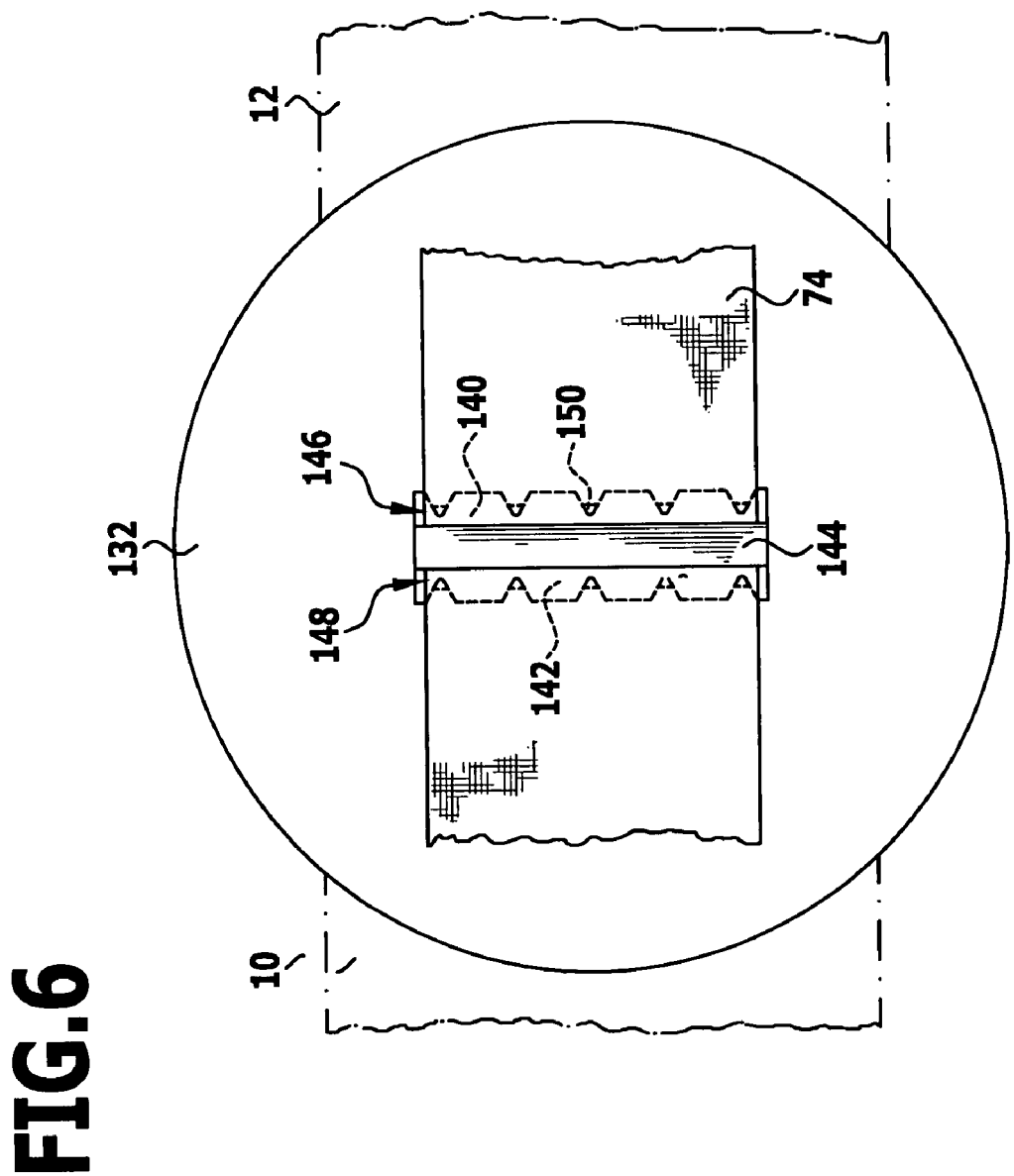

In a third embodiment, which is denoted as a whole by 130 in FIGS. 5 and 6, the inner abutment element 18 is likewise in principle of an identical construction to that described above. An outer abutment element 132 has a convex outer surface 134. Remote from said surface, a surface 136 of the outer abutment element 132 is provided with a toothed wheel ring 138 in the manner described above.

In the outer abutment element 132 two spaced-apart slot-shaped through-openings 140 and 142 are formed in a central region and separated by a bridge element 144. The tension band 74 is passed through these openings 140 and 142.

On the outer abutment element 132 a row of hook elements 146, 148 is formed in the openings 140 and 142, in each case opposite the bridge element 144. A hook 150 of such a row in said case has a steep flank facing the outer surface 134 of the outer abutment element 132 and an inclined flank arranged facing the surface 136.

Through the openings 140 and 142 respective ends of the tension band 74 are threaded, and by tightening the tension band the inner abutment element 18 and the outer abutment element 132 may be drawn towards one another and so the bone plates 10 and 12 may be fixed relative to one another by means of the abutment elements 18 and 132. This fixed position may be secured by hooking the tension band into the hooks 150 of the hook rows 146 and 148.

Given the use according to the invention of a tension band, no application instrument is required for fixing the bone plates 10, 12 between inner and outer abutment element: by tightening the tension band 74 a surgeon may draw the abutment elements towards one another and hence achieve a secure fixation of the bone plates 10 and 12 relative to one another. This fixed position is then secured by hooking-in of the tension band 74, wherein the corresponding hook elements penetrate the structure of the tension band 74. In said case, depending on the application the tension band 74 may be made of an absorbable material or a non-absorbable material.

The invention claimed is:

1. Implant for fixing adjacent bone plates, comprising:
   an inner abutment element for overlapping a separation gap between the bone plates at an inner side of said bone plates;
   an outer abutment element for overlapping the separation gap at an outer side of said bone plates; and
   at least one elastically bendable tension band, each of said at least one tension band having a first free end and a second free end, the first and second free ends being located above an outer surface of the outer abutment element, said at least one tension band being guidable through the outer abutment element in a displaceable manner and adapted such that, when a tensile stress is exerted on the at least one tension band, the inner abutment element and the outer abutment element are drawn towards one another; and
   one or more hook elements associated with each of the first and second free ends for fixing the at least one tension band relative to the outer abutment element;
   wherein:
      the one or more hook elements are formed on the outer abutment element;
      a height of the one or more hook elements is greater than a height of the at least one tension band;
      the at least one tension band is fixable relative to the outer abutment element by penetration of the one or more hook elements into the free ends of the at least one tension band such that, in a fixing position, a hook tip of each of the one or more hook elements penetrates completely through the at least one tension band; and
      at least in an area of the at least one tension band where the penetration occurs, a width of the at least one tension band is at least five times greater than the height of the at least one tension band.

2. Implant according to claim 1, wherein a width of the at least one tension band is in a region of between 25% and 75% of a width dimension of one of said abutment elements.

3. Implant according to claim 1, wherein the at least one tension band is held on the inner abutment element.

4. Implant according to claim 3, wherein the at least one tension band is fastened to the inner abutment element.

5. Implant according to claim 3, wherein the at least one tension band is passed through the inner abutment element.

6. Implant according to claim 5, wherein the at least one tension band is held on the inner abutment element by means of a tension band bend.

7. Implant according to claim 5, wherein the at least one tension band is passed through two spaced-apart openings of the inner abutment element.

8. Implant according to claim 7, wherein the openings are disposed and designed in such a way that:
   a first tension band region and a second tension band region extend through the separation gap and are aligned substantially parallel to each other, and
   the tension band bend is formed between the first tension band region and the second tension band region.

9. Implant according to claim 7, wherein the openings are disposed substantially mirror-symmetrically relative to a center of the inner abutment element.

10. Implant according to claim 7, wherein a spacing of the openings is less than an eighth of a width dimension of the inner abutment element.

11. Implant according to claim 7, wherein edges of the openings are rounded off.

12. Implant according to claim 1, wherein the outer abutment element has one or more openings, through which longitudinal ends of said at least one tension band are passable.

13. Implant according to claim 12, wherein the one or more openings have a deflection edge for deflecting a tension band, so that a tensile force is exertable upon the tension band transversely of a direction of spacing between the inner abutment element and the outer abutment element.

14. Implant according to claim 13, wherein the deflection edge is rounded off.

15. Implant according to claim 12, wherein the one or more openings are disposed and designed in such a way that the at least one tension band is positioned in the separation gap substantially at right angles to the abutment elements.

16. Implant according to claim 1, wherein a tensile force with a transverse component in a first direction is exertable upon the first free end and a tensile force with a transverse component in an opposite direction is exertable upon the second free end.

17. Implant according to claim 1, wherein each of the one or more hook elements have an inclined flank and a steep flank, wherein the steep flank is arranged facing a pulling end of the at least one tension band.

18. Implant according to claim 1, wherein the one or more hook elements comprise a row of spaced-apart hook elements.

19. Implant according to claim 1, wherein the one or more hook elements are disposed on an outer surface of the outer abutment element.

20. Implant according to claim 19, wherein the hook tips of the one or more hook elements are directed away from the outer surface of the outer abutment element.

21. Implant according to claim 1, wherein the one or more hook elements are disposed in an opening of the outer abutment element for the at least one tension band.

22. Implant according to claim 21, wherein the hook tips of the one or more hook elements are orientated transversely of a direction of spacing between the inner abutment element and the outer abutment element.

* * * * *